(12) United States Patent
Wang et al.

(10) Patent No.: US 9,290,769 B2
(45) Date of Patent: Mar. 22, 2016

(54) NITROGEN FIXATION GENE ISLAND SUITABLE FOR EXPRESSING IN PROKARYOTIC AND EUKARYOTIC SYSTEMS

(75) Inventors: Xia Wang, Beijing (CN); Jianguo Yang, Beijing (CN); Li Chen, Beijing (CN); Yun Yang, Beijing (CN); Yiping Wang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 0 days.

(21) Appl. No.: 14/006,189

(22) PCT Filed: Mar. 21, 2012

(86) PCT No.: PCT/CN2012/072709
§ 371 (c)(1),
(2), (4) Date: Sep. 19, 2013

(87) PCT Pub. No.: WO2012/126367
PCT Pub. Date: Sep. 27, 2012

(65) Prior Publication Data
US 2014/0011261 A1    Jan. 9, 2014

(30) Foreign Application Priority Data
Mar. 23, 2011   (CN) .......................... 2011 1 0070755

(51) Int. Cl.
*C12N 15/70* (2006.01)
*C12N 15/52* (2006.01)
*C12N 15/82* (2006.01)

(52) U.S. Cl.
CPC ............... *C12N 15/70* (2013.01); *C12N 15/52* (2013.01); *C12N 15/8261* (2013.01)

(58) Field of Classification Search
None
See application file for complete search history.

(56) References Cited

U.S. PATENT DOCUMENTS 6,548,289 B1   4/2003   Beynon

FOREIGN PATENT DOCUMENTS

| CN | 101016552 A | 8/2007 |
| CN | 101285054 A | 10/2008 |
| WO | WO 03/089640 A2 | 10/2003 |
| WO | WO 2009/013745 A1 | 1/2009 |
| WO | 2012174271 | 12/2012 |

OTHER PUBLICATIONS

Shetty et al., Journal of Biological Engineering, 2008, vol. 2, pp. 1-12.*
Tabor, Current Protocols in Molecular Biology, 1990, 16.2.1-16.2.11.*
Hongxin et al., Science in China: SEries C Life Sciences, 2006, vol. 49, pp. 115-122.*
Imburgio et al., Biochemistry, 2000, vol. 39, pp. 10419-10430.*
Temme, Designing and Engineering Complex Behavior in Living Machines, 2011, permalink: https://escholarship.org/uc/item/1r41x99s.*
BioBricks to help reverse-engineer life, EETimes, 3 pages (2004).
Buchanan-Wollaston et al., Nature, vol. 294, pp. 776-778 (1981).
Cannon et al., Journal of General Microbiology, vol. 93, pp. 111-125 (1976).
Cheng, Biochemical and Biophysical Research Communications, vol. 329, pp. 966-975 (2005).
Cheng, Journal of Integrative Plant Biology, vol. 50, No. 7, pp. 784-796 (2008).
Ditta et al., Plasmid, vol. 13, pp. 149-153 (1985).
Dixon et al., Nature, vol. 260, pp. 268-271 (1976).
Imburgio et al., Biochemistry, vol. 39, No. 34, pp. 10419-10430 (2000).
Imperial et al., Journal of Bacteriology, vol. 158, No. 1, pp. 187-194 (1984).
Jha, The Guardian, 7 pages (2005).
Knight, Idempotent Vector Design for Standard Assembly of Biobricks, MIT Synthetic Biology Working Group, pp. 1-11 (2003).
MacNeil et al., Journal of Bacteriology, vol. 145, No. 1, pp. 348-357 (1981).
Miller, Assay of β-Galactosidase, New York: Cold Spring Harbor Laboratory Press, pp. 352-355 (1972).
Nathans and Smith, Annu. Rev. Biochem., vol. 44, pp. 273-293 (1975).
PCT/CN2012/072709 International Search Report by Shuo Zhao mailed Jun. 21, 2012.
Shetty et al., Journal of Biological Engineering, vol. 2, No. 5, pp. 1-12 (2008).
Zamir, Proc. Natl. Acad. Sci. USA, vol. 78, No. 6, pp. 3496-3500 (1981).
Zhang et al., Acta Biochimica et Biophysica Sinica, vol. 32, No. 6, pp. 620-626 (2000) (with English Abstract).
Zhu, Effect of nifA product on suppression of Nif phenotype of gln mutation and constitutive synthesis of nitrogenase in Klebsiella pneumoniae. Sci. Sin., pp. 688-696 (1983) (with English Abstract).
Arvani, Dissertation to obtain the degree Doctor Philosophiae, pp. 1-117 (2009).
Arvani et al., Journal of Biotechnology, vol. 159, No. 3, pp. 162-171 (2012).
Boddy et al., Journal of the American Chemical Society, vol. 126, No. 24, pp. 7436-7437 (2004).

(Continued)

*Primary Examiner* — Michele K Joike
*Assistant Examiner* — Mindy G Brown
(74) *Attorney, Agent, or Firm* — RatnerPrestia

(57) ABSTRACT

Provided is a nitrogen fixation gene island suitable for expressing in prokaryotic and eukaryotic systems, wherein the prokaryotic nitrogen fixation genes are modified using T7 promoters to make them suitable for eukaryotic expression.

13 Claims, No Drawings

(56) References Cited

OTHER PUBLICATIONS

Drepper et al., Biochemical Society Transactions, vol. 33, Pt. 1, pp. 56-58 (2005).
Extended European Search Report issued Jan. 5, 2015 for European Application No. 12761398.2-1406.
Fischbach and Voigt, Biotechnology Journal, vol. 5, No. 12, pp. 1277-1296 (2010).
Garcia-Rodriguez and Toro, Molecular Plant-Microbe Interactions, vol. 13, No. 6, pp. 583-591 (2000).
Mutka et al., Biochemistry, vol. 45, No. 4, pp. 1321-1330 (2006).
Pfeifer et al., Science, vol. 291, No. 5509, pp. 1790-1792 (2001).
Voigt, Gaining Access: Rebuilding Genetics from the Ground Up, Institute of Medicine Board on Global Health Forum on Microbial Threats, pp. 1-26 (2011).
Watanabe et al., Proceedings of the National Academy of Sciences, vol. 100, No. 17, pp. 9774-9778 (2003).
Zhang et al., Nature Products Reports, vol. 28, pp. 125-151 (2010).
First Chinese Office Action mailed Oct. 28, 2014 in Chinese Application No. 201110070755.5 (with English translation).
Second Chinese Office Action mailed Jul. 6, 2015 in Chinese Application No. 201110070755.5 with English translation).
Sleight et al., Nucleic Acids Research, pp. 1-13 (2010).

* cited by examiner

NITROGEN FIXATION GENE ISLAND SUITABLE FOR EXPRESSING IN PROKARYOTIC AND EUKARYOTIC SYSTEMS

CROSS-REFERENCE TO RELATED APPLICATIONS

This application is a U.S. National Phase Application of PCT International Application PCTICN2012/072709, filed Mar. 21, 2012, which claims priority to Chinese Application No. 201110070755.5, filed Mar. 23, 2011, the contents of which are incorporated herein by reference in their entireties for all purposes.

FIELD OF THE INVENTION

The present invention relates to modification of a regulatory element of a prokaryotic gene and to construction of an expression island that is suitable for eukaryotic expression. More specifically, said prokaryotic gene is a nitrogen fixation gene. Even more specifically, said prokaryote is *Klebsiella pneumoniae*.

BACKGROUND OF THE INVENTION

Nitrogen Fixation

All living organisms require nitrogen. it is a main component of amino acids, nucleic acids (DNA and RNA) and many other important molecules in living cells. However, the majority of organisms cannot utilize nitrogen in the atmosphere directly, and can only utilize nitrogen compounds of certain forms. The processes of forming such nitrogen compounds are collectively referred to as "nitrogen fixation". In nitrogen fixation, nitrogen is combined with other elements and is "fixed" within nitrogen containing compounds.

Agricultural plants are grown in large quantities all over the world, and substantial amount of nitrogen in soil is consumed by these plants every year. If there were no replenishment of nitrogen, its content in the soil would decrease and this would affect the output of the agricultural plants.

In reality, the soil acquires replenishment of nitrogen element via two routes: the application of nitrogen-containing fertilizers, and the biological nitrogen fixation. It was estimated in the 1980s that the nitrogen fertilizers applied every year globally contain around $8\times10^7$ tons of nitrogen, while as much as $4\times10^8$ tons of nitrogen is provided by the nature via biological nitrogen fixation in the mean time.

Thus, if nitrogen fixation mechanism can be applied in food crops like wheat and rice plant to allow them to fix nitrogen on their own, the global requirement of nitrogen fertilizers would be greatly reduced and the agricultural output would be increased. This would be very meaningful in solving global food issues and in protecting the eco-environment.

Nitrogen Fixing Microorganisms

Biological nitrogen fixation is mainly accomplished by nitrogen fixing microorganisms.

Nitrogen fixing microorganism can be divided into two major classes: symbiotic and free-living. Typical symbiotic nitrogen fixing microorganisms include rhizobia that fix nitrogen only when they are in symbiotic relationship with legumes. Free-living nitrogen fixing microorganisms are soil-borne microorganisms that can fix nitrogen independently, mainly bacteria and *Cyanobacterium* (also known as blue-green algae). Common nitrogen fixing bacteria include aerobic *Pasteurella*, anaerobic *Klebsiella*, as well as *Rhodospirillum* and *Chromatium* that are capable of photosynthesis. Currently, the most common free-living nitrogen fixing bacterium that is used as a nitrogen fertilizer is the aerobic *Azotobacter chroococcum*.

Nitrogen Fixation Genes

Among various nitrogen-fixing microorganisms, the most extensively studied one is *Klebsiella pneumoniae*. Its nitrogen fixation genes comprise 17-20 nif genes, in sequence are J, H, D, K, T, Y, E, N, X, U, S, V, W. Z, M, F, L, A, B, and Q. These genes form 7 operons, listed below (Qi Cheng, Perspectives in Biological Nitrogen Fixation Research. *Journal of Integrative Plant Biology*, 2008):

NifJ operon: comprises nifJ gene
NifHDKY operon: comprises nifH, nifD, nifK, and nifY gene
NifENX operon: comprises nifE, nifN, and nifX gene
NifUSVM: operon: comprises nifU, nifS, nifV, and nifM gene
NifF operon: comprises nifF gene
NifLA operon: comprises nifL and nifA gene
NifBQ operon: comprises nifB and nifQ gene The nitrogen fixation system is conserved among all nitrogen fixing microorganisms and the nitrogen fixation genes share very high homology. For example, the nif gene of the nitrogen fixation system of rhizobia is homologous to the nif gene of *K. pneumoniae*.

The Heterogeneous Expression of Nitrogen Fixation Genes of *Klebsiella pneumoniae*

A 24 kb nif nitrogen fixation gene (NCBI Accession number X13303) is cut off from the chromosome of *Klebsiella pneumoniae*, and is ligated as a whole into a vector for transforming *E. coil* (*Escherichia coil*) to confer the host cell the ability of fixing nitrogen (Ray Dixon, Frank Cannon, Construction of a P plasmid carrying nitrogen fixation genes from *Klebsiella pneumoniae*. Nature, 1976). However, a yeast transformed with the same gene produce only some but not all of the proteins of the nitrogen fixing enzymes, and is not able to fix nitrogen (Ada Zamir, Stable chromosomal integration of the entire nitrogen fixation acme cluster from *Klebsiella pneumoniae* in yeast *Proc. NatL Acad. Sci. USA*, 1981). It can then be seen that it is difficult to express prokaryotic nitrogen fixation genes in eukaryotes to allow the biological nitrogen fixation of eukaryotes such as wheat and rice plants.

SUMMARY OF THE INVENTION

The present invention aims at modifying the expression regulatory mechanism of prokaryotic genes to make them suitable for eukaryotic expression. Said prokaryotic genes are preferably nitrogen fixation genes.

DETAILED DESCRIPTION OF THE INVENTION

For better understanding of the present invention the following definitions are provided:

Expression Island

An "expression island", also known as a "regulation island", is a collection of multiple regulatory elements and multiple genes, wherein each regulatory element regulates transcription and/or expression of one or more genes. In the case of prokaryotic genes, an expression island can be one or more operons with regulatory elements. In a preferred embodiment of the invention, in one aspect, the regulation by said regulatory element is independent of the host's intrinsic expression system, i.e. it neither affects nor is affected by the host's expression system; in another aspect, each one of the regulatory elements of the island is independent of other regulatory elements within the same island (if any), thus allowing different genes in the island to he expressed at different levels to optimize the function of each gene product.

In the expression island of the present invention, said regulatory element is preferably not a natural regulatory element of said genes or said operons, more preferably said regulatory element is a T7 promoter selected from: T7wt, T7M4, T7M5, T7M6, T7M7, and T7M8, as well as any other T7 variants active as a T7 promoter with its strength different from the wild-type promoter. In a preferred embodiment of the present invention, an expression island is composed of BioBrick® parts. More preferably, said BioBrick® part consists of genes of interest or operons of interest that carry T7 promoters, such as multiple prokaryotic nitrogen fixation genes with different T7 promoters.

In a specific embodiment, the multiple genes in the expression island are selected from the following nitrogen fixation genes: nifJ, nifH, nifD, nifK, nifT, nifY, nifE, nifN, nifX, nifU, nifS, nifV, nifW, nifZ, nifM, nifF, nifL, nifA, nifB, and/or nifQ. In another specific embodiment, said expression island does not contain the following nitrogen fixation genes: nifT, nifY, nifX, nifU, nifS, nifV, nifW, nifZ, nifL, nifA, and/or nifQ. In yet another specific embodiment, said nitrogen fixation genes are in the form of a natural operon expect that the promoters in the natural operon are replaced with T7 promoters. In still another specific embodiment, said operons are T7wt+nifJ, T7wt+nifHDKY, T7M5+nifENX, T7M5++nifUSVM, T7M6+nifF, and/or T7M6+nifBQ.

BioBrick®

The term "BioBrick®" is a trademark of BioBricks Foundation, BioBrick® parts are DNA sequences in the form of standard biological parts, in which each standard part has the same "prefix" (SEQ ID NO: 45) and "postfix" (SEQ ID. NO: 46), shown as follows:

```
5' --gca GAATTC GCGGCCGC T TCTAGA G --insert-- T ACTAGT A GCGGCCG CTGCAG gct--
    --cgt CTTAAG CGCCGGCG A ACATCT C ---------- A TGATCA T CGCCGGC GACGTC cga--
         EcoRI   NotI     XbaI              SpeI    NotI   PstI
```

As BioBrick® parts share a common interface, they are often introduced into living cells such as E. coil cells to construct new biological systems. Thus they are frequently used in the fields of synthetic biology, nanotechnology and so on. See, for example, "Knight, T. (2003), Idempotent Vector Design for Standard Assembly of Biobricks. *MIT Synthetic Biology Working Group*; From the cells up, *The Guardian*, 10 Mar. 2005; BioBricks to help reverse-engineer life, *EETimes*, 11 Jun. 2004", The Feasibility of Constructing a BioBrick® Part The *K. pneumoniae* nif genes were reported to he transformed as a whole into *E. coil* directly (see Background Art part). However, there is no report on that the genes are split into multiple operons and then re-combined to express nitrogen fixation enzymes in *E. coli*.

The nitrogen fixation genes, particularly the 24 kb nif gene of *K. pneumoniae* (NCBI X13303) carried on the plasmid. pRD1, were cloned by the applicant as individual operons containing natural promoters. Each of the operons was then introduced into a conventional plasmid, such as pBS, that contain both prefix and postfix structures of a BioBrick® part, These operons in the form of BioBrick® parts were then introduced one after another into a multicopy vector, such as pACYC184. Expression was achieved in *E. coli*. It is shown that, after individual digestion by restriction enzymes and subsequent ligation into vectors, these operons expressed nitrogen fixing enzyme activity in *E. coil*.

Another characteristic of the present invention is that, each prokaryotic operon can be manipulated individually, and need not to he manipulated together with other operons that naturally work together. As an example, each of the above-mentioned operons in the form of BioBrick® parts may comprise not only the common prefix and postfix of BioBrick® parts, but also an unique restriction site (see e.g. Table 2 below). In this way, each operon can he selectively manipulated, e.g. enzymatically digested. The unique restriction site can be chosen by a skilled artisan, and is not limited to those illustrated in the examples of the present application.

By individual manipulation, several operons in the form of BioBrick® parts can be introduced into a multicopy plasmid in any sequential order. For example, the restriction site unique to nifJ in the Examples described herein is a ScaI site, thus the ScaI enzyme is used to introduce the relevant operon into a multicopy plasmid, pACYC184, without affecting other operons. This introduction could he the first or optionally, the second, third, fourth, fifth, sixth, or seventh among the introductions of multiple operons. The structure of final combination is determined by the particular sequential order of the introductions.

T7 Transcription System

The T7 transcription system comprises a promoter region and a RNA polymerase region. It is currently the most commonly used and most effective system for gene expression in *E. coil*. T7 transcription system can also express gene effectively in eukaryotes, such as in yeast mitochondria.

As a single monomer protein, T7 RNA polymerase acts independently via a 17 bp promoter, and thus is simple to be regulated.

T7 promoter is relatively conserved among various species, As shown below, it can be divided into two structural/functional regions: the −17~−5 binding region responsible for binding with T7 RNA polymerase; and the −4~+6 initiation region responsible for transcription initiation:

(SEQ ID NO: 47)

```
              -15      -10       -5     +1    +5
T7  (17)  T A A T A C G A C T C A C T A T A G G G A G A
          ----------binding region---------- ----initiation region----
```

Several variants of T7 promoter have been obtained by mutation of the nucleotides within the promoter region. In vitro transcription assays showed that the strength of theses variants are different from each other and different from the wild-type T7 (Diane Imburgio, Studies of Promoter Recognition and Start Site Selection by T7 RNA Polymerase Using a Comprehensive Collection of Promoter Variants *Biochemistry*, 2000, 34 (34), 10419-10430, 2000). The variants are summarized as follows:

| Variant Name | Abbreviation | Mutation | Relative Strength |
|---|---|---|---|
| T7M4 | T-4A | −4 position, T to A | 0.08 |
| T7M5 | T-2G | −2 position, T to G | 0.49 |
| T7M6 | T-4G | −4 position, T to G | 0.23 |

-continued

| Variant Name | Abbreviation | Mutation | Relative Strength |
|---|---|---|---|
| T7M7 | A-15T | −15 position, A to T | 0.71 |
| T7M8 | A-15G | −15 position, A to G | 0.11 |

"Relative strength" refers to the promoter strength in relative to the wild-type T7 (T7wt) strength, which is designated as 1.0.

By using a T7 system that can express genes in both prokaryotic and eukaryotic systems, one could take full advantage of E. coil, the well-recognized genetic manipulation platform, to construct a nitrogen fixation gene expression system that totally depends on T7 RNA polymerase, and then transfer the system into an eukaryotic system after demonstrating its nitrogen fixation activity in experiments. Such a system shuttling between prokaryotes and eukaryotes will play a vital role in the final construction of a "nitrogen fixing island" that allows eukaryotes to fix nitrogen independently (for example: the system can be firstly constructed and tested for function in prokaryotes and then transferred to eukaryotes. This could greatly reduce the complexity of research works).

Replacement of Promoters

Regarding the report that the expression of all nitrogen fixation genes of K. pneumoniae in yeast does not confer the host the ability to fix nitrogen, the inventors think one of the possible reasons is that the prokaryotic expression regulation system of K. pneumoniae is not compatible with the eukaryotic cellular machinery.

After verifying that the nitrogen fixation system of K. pneumoniae is not necessarily genetically operated as a whole, but rather operated as separating operons, it appears to the inventors that to solve the problem of regulating eukaryotic expression, the natural promoters of such prokaryotic operons can be replaced with promoters that are able to work in both prokaryotic cells and eukaryotic cells, such as T7 promoter, To this, each of the nif promoters of K. pneumoniae can be introduced into a plasmid with a specific marker, and the strength of said nif promoter can he determined by measuring the expression level or activity of the marker. Said specific marker is for example a beta-galactosidase gene, or any other conventional markers. The strength of a naturally-occurring promoter determined in this way is compared with the strength of T7 promoters recorded in the prior art, and several (e.g. 2 or 3) T7 promoters with comparable strength are selected for testing. In this way, T7 promoters that perform well in the whole nitrogen fixation system can be selected.

nif Genes or Operons in the Expression Island

Regulation of nif transcription include the general regulation mechanism mediated by genes outside the nif gene cluster (e.g. ntrA, ntrB, and ntrC), and the specific regulation mediated by nifL and nifA genes within the nif gene cluster. Generally, genes such as ntrB and ntrC respond to outside nitrogen source and regulate nifL and nifA, which in turn regulate other nitrogen fixation genes.

In one embodiment of the present invention, the expression island comprises nifLA, operon with its natural promoter unreplaced by T7 promoter, see for example pKU7181. Yet in another embodiment, the expression island does not comprise nifLA operon, see for example pKU7180. Experiments showed that, the expression island of the invention can still express nitrogen fixing activity in the absence of nifLA operon. Further experiments showed that, the nitrogen fixation enzymes expressed by the expression island of the present invention are not affected by known factors, such as temperature, nitrogen availability, NtrC and σ54 factor, that affect the expression of natural prokaryotic nitrogen fixing enzymes, but rather only affected by the regulatory factor of T7: isopropyl-β-D-thiogalactoside (IPTG) (e.g. see Table 11 and 12 below). It can be seen that the expression island of the present invention successfully bypasses the natural regulatory pathways modulated by nifL, and nifA, making the expression of nitrogen fixation genes simpler and easier to be controlled.

However, the expression island of the invention does not necessarily comprise all of the prokaryotic nitrogen fixation genes or all of the nitrogen fixing operons. For example, it is known that with deletion of nifQ gene, K. pneumoniae is still active in nitrogen fixation if exogenous molybdenum is provided (Journal of Bacteriology, V158 (1): 187-194, 1984). Also for example, it is shown in the present application that, E. coli in absence of nifL and nifA genes (i.e. nifLA operon) is still active in nitrogen fixation. Also for example, it has been found that nifH gene products overlap in terms of function with Chlamydomonas reinhardtii homolog, chlL (Qi Cheng, The Klebsiella pneumoniae nitrogenase Fe protein gene (nifH) functionally substitutes for the chlL gene in Chlamydomonas reinhardtii, BBRC, 2005). Therefore, the expression island of the invention is able to express nitrogen fixing gene in absence of one or more genes in the prokaryotic nitrogen fixation system. For example, those nitrogen fixation genes not essential in a relevant host (such as an eukaryotic host) can be deleted in the expression island, or be replaced by functional products inherent to the host, to render function of one or more prokaryotic nitrogen fixation genes (e.g. nif genes). This further simplifies the structure of the expression island of the present invention.

More specifically, the present invention relates to the following:

One aspect of the invention relates to an individual prokaryotic nitrogen fixing operon, which does not comprise a natural promoter but comprises a T7 promoter. In a preferred embodiment, said T7 promoter is selected from the group consisting of: T7wt, T7M4, T7M5, T7M6, T7M7, and T7M8, as well as any other T7 variants having T7 promoter activity with strength different from the wild-type promoter. In a more preferred embodiment, the prokaryotic nitrogen fixation genes are nitrogen fixation genes of K. pneumoniae, such as those shown in NCBI X13303. in an even more preferred embodiment, the operon of the present invention is selected from the group consisting of: T7wt+nifJ, T7wt+nifHDKY, T7M5+nifENX, T7M5+nifUSVM, T7M6+nifF, and T7M6+nifBQ.

Another aspect of the present invention relates to an expression island, Which comprises one or more regulatory elements and one or more genes. In one preferred embodiment, said regulatory element is a T7 promoter; in case that there are several promoters, said several promoters can be identical to or different from each other. In another preferred embodiment, said genes are in the form of a prokaryotic nitrogen fixing gene operon with no natural promoter but controlled under T7 promoters. In a specific embodiment, operons comprising T7 promoters in the expression island of the present invention are combined in the form of BioBrick® parts. In another specific embodiment, an operon in the expression island of the invention has a restriction site different from those in other operons; thus each of the operons can be manipulated individually. In a particularly preferred embodiment, the expression island of the present invention comprises one or more operons selected from the group consisting of: T7wt+nifJ, T7wt+nifHDKY, T7M5+nifENX, T7M5+nifUSVM, T7M6+nifF, and T7M6+nifBQ.

The prokaryotic nitrogen fixing operon or the expression island of the present invention can be carried on a plasmid. Preferably said plasmid is a multicopy plasmid so that the nitrogen fixation genes can be expressed at high level.

The present invention in another aspect relates to a multicopy plasmid comprising a T7 polymerase gene. In one specific embodiment, said plasmid is pBR322. Such multicopy plasmid of the present invention can express T7 RNA polymerase at high level, so as for the regulated prokaryotic genes (e.g. prokaryotic nitrogen fixation genes) to be appropriately expressed.

Another aspect of the present invention relates to an expression system, which comprises a plasmid containing the prokaryotic nitrogen fixing gene operon or the expression island of the present invention, and a plasmid containing the T7 RNA polymerase gene of the present invention. Said expression system can be expressed in both prokaryotic cells and eukaryotic cells to produce nitrogen fixing enzyme activity. Accordingly, the present invention also relates to a host cell, which comprises the operon, the expression island, the plasmid, or the expression system of the present invention.

Another aspect of the present invention relates to a method for constructing an eukaryotic expression island, said method comprises: determining the promoter strength of each gene in a group, replacing the promoters with identical or different T7 promoters based on the determined strength, and combining all of the genes with Ti promoters to form an expression island. Preferably, said method includes transferring the combined genes into an appropriate host for expression. In a preferred embodiment, said T7 promoters are selected from the group consisting of: T7wt, T7M4, T7M5, T7M6, T7M7, and T7M8, as well as any other T7 variants having T7 promoter activity with the strengths different from the wild-type promoter.

The present invention in still another aspect relates to the use of T7 promoter in coordinating the expression of multiple genes. Specifically, said expression is the expression in prokaryotic cells or prokaryotic organisms, or the expression in eukaryotic cells or eukaryotic organisms. In a preferred embodiment, said T7 promoters are selected from the group consisting of: T7wt, T7M4, T7M5, T7M6, T7M7, and T7M8, as well as any other T7 variants having T7 promoter activity with the strengths different from the wild-type promoter.

EXAMPLES

Materials:
Bacteria Strains:
E. coli strain JM109, DH5α and BL21 (DE3) were all purchased from Beijing TransGen Biotech Co., LTD., where E. coli JM109 and BL21 (DE3) were mainly used to test the activities of nitrogen fixing enzymes; E. coli DH5α is mainly used to confirm the sequence of the cloned products. In addition, E. coli TH1 has the genotype F–, σ54; E. coli WJ9 has the genotype F–, ntrC; E. coli TP2006 has the genotype F–, xyl, cya, crp-39, lacΔx74, argH1, glp, they were all kept in the present laboratory, but can be constructed via conventional techniques by a skill artisan.

Plasmids:
Several plasmids used in the present application were commercially available. For example, pET28a can be purchased from Novagen, pACYC184 is available as ATCC 37033. Other plasmids were recited in the prior art, see, for example "Gary Ditta, Plasmids related to the broad host range vector, pRK290, useful for gene cloning and for monitoring gene expression. *Plasmid*, 1985" for pGD926; see "Zhu JB. Effect of nifA product on suppression of Nif phenotype of gln mutation and constitutive synthesis of nitrogenase in *Klebsiella pneumoniae*. Sci. Sin. 1983" for pST1021; see "Ray Dixon, Frank Cannon, Construction of a P plasmid carrying nitrogen fixation genes from *Klebsiella pneumoniae* . *Nature*, 1976" for pRD1. Plasmids of the present invention are illustrated in Table 1 below.

TABLE 1

| Plasmid | Description |
|---|---|
| pUC18 | ColE1, lacZ', Ap$^R$ (ampicillin resistance) |
| pBR322 | colE1, Ap$^R$, Tc$^R$ |
| pBluescript-SK | colE1, lacZ', Ap$^R$ |
| pet28a | colE1, containing T7 promoter and terminator, lacI, Km$^R$ |
| pGD926 | lacZYA translation fusion vector, Tc$^R$ |
| pST1021 | pACYC 184 derivative plasmid, constitutively express nifA, Cm$^R$ |
| pACYC184 | P15A, Cm$^R$(chloramphenicol resistance) |
| pRD1 | P-class R factor, nif$^+$, his$^+$, Km$^R$(kanamycin resistance), Cb$^R$(carbenicillin resistance), Tc$^R$(tetracyclin resistance) (gift from Ray Dixon laboratory) |
| pBS-nifHDKY | XbaI-SpeI fragment of nifHDKY fused to pBS, Ap$^R$ |
| pBS-nifJ | XbaI-SpeI fragment of nifJ fused in the form of a biobrick part to pBS, Ap$^R$ |
| pBS-nifENX | XbaI-SpeI fragment of nifENX fused in the form of a biobrick part to pBS, Ap$^R$ |
| pBS-nifUSVM | XbaI-SpeI fragment of nifUSVM fused to pBS, Ap$^R$ in the form of a biobrick part |
| pBS-nifBQ | XbaI-SpeI fragment of nifBQ fused in the form of a biobrick part to pBS, Ap$^R$ |
| pBS-nifF | XbaI-SpeI fragment of nifF fused in the form of a biobrick part to pBS, Ap$^R$ |
| pBS-nifLA | XbaI-SpeI fragment of nifLA fused in the form of a biobrick part to pBS, Ap$^R$ |
| pKU7017 | the above-mentioned 7 nif operons fused in the form of biobrick parts to pACYC184, Cm$^R$ |
| pKU7021 | NifF operon without its natural promoter and terminator, fused to pet28a with T7 promoter mutation T-4G, Km$^R$ |
| pKU7023 | NifHDK operon without its natural promoter and terminator, fused to pet28a, Km$^R$ |
| pKU7027 | NifJ operon without its natural promoter and terminator, fused to pet28a, Km$^R$ |
| pKU7026 | NifBQ operon without its natural promoter and terminator, fused to pet28a with T7 promoter mutation T-4G, Km$^R$ |
| pKU7051 | NifUSVM operon without its natural promoter and terminator, fused to pet28a with T7 promoter mutation T-2G, Km$^R$ |
| pKU7053 | NifENX operon without its natural promoter and terminator, fused to pet28a with T7 promoter mutation T-2G, Km$^R$ |
| pKU7181 | pet28a version of nif gene fused in the form of a biobrick part to pACYC184, Cm$^R$ |
| pKU7093 | T7 RNA polymerase gene fused to pBR322, Ap$^R$ |
| pKU800 | nifB promoter (PnifB) fused into lacZYA of pGD926, Tc$^R$ |

TABLE 1-continued

| Plasmid | Description |
|---------|-------------|
| pKU801 | PnifE fused into lacZYA of pGD926, Tc$^R$ |
| pKU802 | PnifF fused into lacZYA of pGD926, Tc$^R$ |
| pKU803 | PnifH fused into lacZYA of pGD926, Tc$^R$ |
| pKU804 | PnifJ fused into lacZYA of pGD926, Tc$^R$ |
| pKU805 | PnifLA fused into lacZYA of pGD926, Tc$^R$ |
| pKU806 | PnifU fused into lacZYA of pGD926, Tc$^R$ |

Other Reagents:

Various restriction enzymes were purchased from TaKaRa Inc. and New England Biolabs Inc. DNA polymerase (EasyTag and EasyPfu), dNTP, and DNA marker were all purchased from Beijing TransGen Biotech Co., LTD. T4 DNA ligase and alkaline phosphatase were purchased from Fermentas. Normal DNA product purification kit, normal plasmid mini-prep kit and argarose gel extraction kit were purchased from TianGen Biotech Co., Ltd (Beijing). Antibiotics were purchased from Beijing Jiangchenhongwei Co., Ltd. (Beijing). Other common reagents were purchased from China National Medicines Co., Ltd. (Beijing), Sigma-Aldrich China (Shanghai) and etc.

Example 1

In this example, seven *K. pneumonia* nif operons were re-combined in the form of BioBrick® parts and used to transform *E. coli* strain JM109. The nitrogen fixing enzyme activities of the transformants were determined using Acetylene Reduction Assays.

Firstly, the following primers were designed based on the sequence of the 24 kb nif genes published by NCBI (X13303):

TABLE 2

| Primer Name | Primer Sequence (5'-3') | Relevant Restriction Sites |
|-------------|-------------------------|----------------------------|
| NifHDKY(1) | gcaGAATTC GCGGCCGC TCTAGA TACGTA tgaagaga gtcgccgcgc ag (SEQ ID NO: 1) | EcoRI/NotI/XbaI/ SnaBI |
| NifH DKY(2) | gctCTGCAG GCGGCCG ACTAGT TACGTA GCAACAAGCACAAAACAGGGA (SEQ ID NO: 2) | PstI/NotI/SpeI/ SnaBI |
| NifJ(1) | gcaGAATTC GCGGCCGC TCTAGA AGTACT GTTATTTGTCGCCGCGCAGG (SEQ ID NO: 3) | EcoRI/NotI/XbaI/ScaI |
| NifJ(2) | gctCTGCAG GCGGCCG ACTAGT AGTACT CTAAAGGCCCGCTACTCCTCG (SEQ ID NO: 4) | PstI/NotI/SpeI/ScaI |
| NifUSVM(1) | gcaGAATTC GCGGCCGC TCTAGA GTTTAAAC gc aggagcagga gtggcatg (SEQ ID NO: 5) | EcoRI/NotI/XbaI/PmeI |
| NifUSVM(2) | gctCTGCAG GCGGCCG ACTAGT GTTTAAAC CGAGGCTACCCGCACAGTCC (SEQ ID NO: 6) | PstI/NotI/SpeI/PmeI |
| NifENX(1) | gcaGAATTC GCGGCCGC TCTAGA CCTAGG gcttcttgat gcgcctaacc (SEQ ID NO: 7) | EcoRI/NotI/XbaI/AvrII |
| NifENX(2) | gctCTGCAG GCGGCCG ACTAGT CCTAGGG TCACAGAAACGACACGGCTA (SEQ ID NO: 8) | PstI/NotI/SpeI/AvrII |
| NifLA(1) | gcaGAATTC GCGGCCGC TCTAGA CTTAAG TGTTGCGCTCCTGTCGGAAA (SEQ ID NO: 9) | EcoRI/NotI/XbaI/AflII |
| NifLA(2) | gctCTGCA GGCGGCCG ACTAGT CTTAAG ACAGTCGCGGCATGGTGATATC (SEQ ID NO: 10) | PstI/NotI/SpeI/AflII |
| NifBQ(1) | gcaGAATTC GCGGCCGC TCTAGA GCTAGC CGACTGTGAAGCCTTATGTG (SEQ ID NO: 11) | EcoRI/NotI/XbaI/ NheII |
| NifBQ(2) | gctCTGCAG GCGGCCG ACTAGT GCTAGC GCTACTCAAAACAGGCGCTG (SEQ ID NO: 12) | PstI/NotI/SpeI/ NheI |
| NifF(1) | gcaGAATTC GCGGCCGC TCTAGA atttaaat TTCAGGGTCATCGCAAACTC (SEQ ID NO: 13) | EcoRI/NotI/XbaI/SwaI |
| NifF(2) | gctCTGCAG GCGGCCG ACTAGT atttaaat GTTAACGCCTACAGCACGGTG (SEQ ID NO: 14) | PstI/NotI/SpeI/SwaI |

The primers were dissolved in ddH$_2$O to a final concentration of 10 µmol/L.

Plasmid pRD1 carries the whole 24 kb X13303 sequence. This plasmid was used as a temple for PCR amplification in the following reaction systems using the primers as shown in Table 2: 5µl 10×EasyPfu DNA Polymerase Buffer, 4 µl 2.5 mM dNTP, 2 µl 10 µM primer 1 of one of the above-mentioned operons, 2 µl 10 µM primer 2 of said operon, 1 µl pRD1 template, 0.5 µl EasyPfu DNA Polymerase (2.5 U/µl), and suitable amount of ddH2O to bring a final volume of 50 µl. The reaction is as follows: pre-denaturation at 95° C. for 5 min; then 30 cycles of: denaturation at 95° C. for 1 min, annealing at 55° C. for 45 s, extension at 72° C. (5 min for nifHDKY operon, 5 min for nifUSVM operon, 4 min for nifJ operon, 3 min for nifLA operon, 2.5 min for nifBQ operon, 4 min for nifENX operon, and 0.5 min for nifBQ operon); finally, extension at 72° C. for 10 min. In this way, amplified product of each nif operon was obtained. These products were purified with normal DNA Product Purification Kit of Tian-Gen Company.

1 µl EcoRV fragment of a pBS plasmid (with the universal prefix and postfix of a BioBrick® part), together with 7 µl of one of the PCR products of nif operons obtained as mentioned-above were ligated by 1 µl T4 DNA ligase in 1 µl of 10×T4 DNA ligation buffer at 22° C. for 1 h.

The products of the above-mentioned ligation were used to transform E. coli DH5α. Specifically, 5 µl ligation product was added into 50 µl ice-chilled competent cells, mixed evenly, and ice-bathed for 30 min; water-bathed at 42° C. for 45 s; ice-bathed briefly for 1-2 min; 500 µl of LB medium pre-warmed to 37° C. were then added into each tribe, which was then shaker incubated at 37° C. for 45 min, 40 µl X-gal was added into 100µl transformed competent cells and mixed evenly. The mixture was then plated onto a LB plate that contains corresponding antibiotics and was pre-warmed to 37° C. The plate was then air-dried, inverted and incubated at 37° C. for 12-16 h until the bacterial colonies appear, where white colonies being the transformants and blue colonies being the products of self-ligation. The plasmids were extracted from the white colonies and undergo restriction digestion to ensure that the nif genes were indeed inserted into the pBS plasmid.

Primers M13F and M13R were used to determine that the nif genes cloned into the pBS plasmid have the correct sequences:

```
M13F: 5'GTAAAACGAC GGCCAGTG 3' (SEQ ID NO: 15)

M13R: 5'GGAAACAGCT ATGACCATG3' (SEQ ID NO: 16)
```

The above-mentioned pBS-nifJ were digested with both XbaI and SpeI, and then ligated with T4 ligase into a XbaI-fragment of pACYC184. The ligation product was used to transform E. coli DH5α, and the obtained single colonies of the transformants were PCR verified with primers NifJ(1) and NifJ(2) shown in Table 2. The positive clones were amplified, and the plasmids extract were verified via restriction digestion. The appropriately digested plasmid was named pKU7001, which carries a nifJ gene.

Because XbaI and SpeI are isocaudomers, the above-mentioned ligation led to a restriction site that was no longer cleavable, therefore pKU7001 remained a unique XbaI site, nifENX was ligated into pKU7001 to obtain pKU7002 according to the same method of cloning pKU7001. In the same manner, all of the 7 nif operons in their respective BioBrick® parts were ligated into pACYC184, resulting in a plasmid named pKU7017. This plasmid carries all of the 7 nif operons combined in the forms of BioBrick® parts.

Plasmid pKU7017 was used to transform E. coil JM109, and the activity of nitrogen fixation enzymes were determined using acetylene reduction assay as described below: a strain to be tested was activated on solid LB plates for overnight, transferred into a tube containing 3 mL medium and grown at 37° C. for overnight. 1 mL of the culture was 1:20 diluted and transferred into a flask containing 20 ml corresponding medium and grown at 37° C. until OD600=0.7-0.8. The culture was centrifuged and the pellet was re-suspended in a glutamate-containing medium until about OD=1.0. 2 ml of the culture was 1:5 diluted and added into a tube, which became anaerobic by three repeated cycle of exhausting air and filling with argon. Each tube was injected with 2 ml of acetylene gas, and stood still for 4-24 hours at 30° C., during which the amount of acetylene was determined by gas chromatography using acetylene standard (Beijing Zhaoge Gas Co,. Ltd.) as a reference, The result is shown in the table below:

TABLE 3

| Strain | Nif Genotype | Nitrogen Fixing Enzyme Activity (nmol C$_2$H$_4$/min/mg of protein) |
|---|---|---|
| K. pneumoniae | Nif$^+$ | 771.7 |
| JM109 | nif$^-$ | 0.9 |
| JM109(pKU7017) | Nif$^+$ | 229.2 |

The above results show that, after the 7 nif operons of K. pneumoniae being re-combined in the form of BioBrick® parts, the activities of the nitrogen fixing enzymes expressed in E. coil are not affected. Furthermore, all the 7 operons in BioBrick® form are indeed capable of being re-combined into a multicopy plasmid, such as a plasmid with a copy number of about 20, and retain their genetic stabilities.

Example 2

Determination of β-Galactosidase Activities Driven by nif Promoters

Each of the nif promoters was separately cloned in to a plasmid pGD926 to form a Pnif::lacZ fusion, and then was transformed into a TP2006(cya-) strain that carryies a pST1021 plasmid (capable of constitutively expressing nifA gene). The β-galactosidase activity was determined (as Miller Units) in a M63 minimal medium with no exogenous supply of cAMP, according to Miller's method (Miller, J. H., *Experiments in Molecular Genetics*, New York: Cold Spring Harbor Laboratory Press, 1972).

TABLE 4

| Plasmid (nif promoter) | β gal activity | Relative Strength |
|---|---|---|
| pku800(nifBQ) | 6209 ± 152 | 0.12 |
| pku801(nifENX) | 22235 ± 256 | 0.43 |
| pku802(nifF) | 10397 ± 184 | 0.20 |
| pku803(nifHDKY) | 38388 ± 326 | 0.74 |
| pku804(nifJ) | 51933 ± 378 | 1.00 |
| pku805(nifLA) | 1347 ± 24 | 0.03 |
| pku806(nifUSVM) | 9209 ± 138 | 0.18 |

Relative Strength: the strength of other promoters as compared with the strength of nifJ which gives the strongest activity and is set as 1,0.

The $M_{63}$ medium consists of (per 100 ml):

| Liquid 5x$M_{63}$ Salts | 20 ml→1x | Autoclave Sterilized |
| --- | --- | --- |
| 20% Sugar | 2 ml→0.4% (Glycerol→0.4%) | Low pressure Sterilized |
| 1% AA | 1 ml→0.01% | Filter Sterilized |
| 2M $(NH_4)_2SO_4$ | 1 ml→20 mM | Autoclave Sterilized |
| 1M $Mg_2SO_4$ | 100 μl→1 mM | Autoclave Sterilized |
| 10 mg/ml $VB_1$ | 10 μl→10 μg/ml | Filter Sterilized |

Wherein 5x$M_{63}$ Salts consists of (per 100 ml):

| $KH_2PO_4$ | 6.8 g |
| --- | --- |
| $FeSO_4 \cdot 7H_2O$ | 0.25 mg | dissolved in 100 ml dd$H_2O$, and pH adjusted to 7.0 using solid KOH.

Example 3

Construction of Plasmid pKU7180 and Plasmid pKU7181 pKU7180 is pKU7017 with the promoters of all operons being replaced by T7 promoters. pKU7181 is identical to pKU7180 except that it does not contain nifLA.

3.1 Point Mutation of pET28a Plasmid

According to the determined β-gal activities, the following primers were used in PCR to mutate the wild-type T7 promoter in pET28a into T7M4, T7M5, T7M6, T7M7, and T7M8 respectively:

TABLE 5

| Primer Name | Primer Sequence (5'-3') | Mutation |
| --- | --- | --- |
| T7M4(1): | GAAATTAATACGACTCACAATAGGGGAATTGTGAGT (SEQ ID NO: 17) | -4A |
| T7M4(2): | CTCACAATTCCCCTATTGTGAGTCGTATTAATTTCT (SEQ ID NO: 18) | -4A |
| T7M5(1): | ATTAATACGACTCACTAgAGGGGAATTGTGAGCGGT (SEQ ID NO: 19) | -2G |
| T7M5(2): | CCGCTCACAATTCCCCTCTAGTGAGTCGTATTAATT (SEQ ID NO: 20) | -2G |
| T7M6(1): | AAATTAATACGACTCACgATAGGGGAATTGTGAGCT (SEQ ID NO: 21) | -4G |
| T7M6(2): | GCTCACAATTCCCCTATCGTGAGTCGTATTAATTTT (SEQ ID NO: 22) | -4G |
| T7M7(1): | CCCTATAGTGAGTCGTAaTAATTTCGCGGGATCGAA (SEQ ID NO: 23) | -15T |
| T7M7(2): | TCGATCCCGCGAAATTAtTACGACTCACTATAGGGA (SEQ ID NO: 24) | -15T |
| T7M8(1): | CCCTATAGTGAGTCGTACTAATTTCGCGGGATCGAA (SEQ ID NO: 25) | -15G |
| T7M8(2): | TCGATCCCGCGAAATTAGTACGACTCACTATAGGGA (SEQ ID NO: 26) | -15G |

The PCR products were digested with DpnI at 37° C. for 2 h, and transformed into E. coli. Positive clones were sent for commercial sequencing.

3.2 Cloning of Individual nif Genes Carrying No Promoters

The following primers were designed based on the sequence of X13303. Each nif operon with no promoter was PCR amplified as described in Example 1. The PCR products were purified and ligated into the cloning vector pBS.

TABLE 6

| Primer Name | Primer Sequence (5'-3') | Restriction Site |
| --- | --- | --- |
| T7NifHDKY(1): | gcTCTAGACACTCAACAACAGGAGAAGTC (SEQ ID NO: 27) | XbaI |
| T7NifHDKY(2): | cccAAGCTTGCAACAAGCACAAAACAGGGATTA (SEQ ID NO: 28) | HindIII |
| T7NifJ(1): | gcTCTAGA CAACTGGGTT TGCCGCTTAT (SEQ ID NO: 29) | XbaI |
| T7NifJ(2): | cccAAGCTTcctgctggatacgctgctta (SEQ ID NO: 30) | HindIII |
| T7NifUSVM(1): | gctctagaTGAACCGCGCCCCGGCGTTT (SEQ ID NO: 31) | XbaI |
| T7NifUSVM(2): | cccAAGCTT CGAGGCTACCCGCACAGTCC (SEQ ID NO: 32) | HindIII |
| T7NifENX(1): | gcTCTAGA CCTCATCCCCCACCGTCAAC (SEQ ID NO: 33) | XbaI |
| T7NifENX(2): | cccAAGCTT GGATGTTGACGGAAAACGCC (SEQ ID NO: 34) | HindIII |
| T7NifBQ(1): | gcTCTAGA GGTATCGCCCAACCACGAAG (SEQ ID NO: 35) | XbaI |
| T7NifBQ(2): | cccAAGCTT CGAAGACGTCGCATAATCAC (SEQ ID NO: 36) | HindIII |

TABLE 6-continued

| Primer Name | Primer Sequence (5'-3') | Restriction Site |
|---|---|---|
| T7NifF(1): | gc<u>TCTAGA</u> GCGAGAACGC GTATTTTCAA (SEQ ID NO: 37) | XbaI |
| T7NifF(2): | ccc<u>AAGCTT</u>CTACAGCACGGTGCGTTTAA (SEQ ID NO: 38) | HindIII |

Note:
The restriction enzyme listed in the third column has the restriction site as underlined in the second column.

3.3 Replacement of the nifENX Promoters into T7wt, T7M4, T7M5, T7M6, T7M7, and T7M8 Respectively pET28a series plasmids carrying T7wt, T7M4, T7M5, T7M6, T7M7, and T7M8 respectively were digested with restriction enzymes XbaI/HindIII, and ligated with XbaI/HindIII-digested pBS vectors carrying the nifENX operon but no promoter. A series of pET28a, plasmids were thus obtained that carry nifENX with different T7 promoter 3.4 Replacement of nifENX Operon in pKU7017 with the nifENX Operons Carrying T7 Promoters The above-mentioned pET28a plasmids that carry nifENX operons with different T7 promoters were used as templates for PCR amplification as described in Example 1, using the following primers. The amplified products were ligated into the pBS vectors, and confirmed by sequencing.

TABLE 7

| Primer Name | Primer Sequence (5'-3') | Restriction Site |
|---|---|---|
| T7P-AvrII: | gc <u>cctagg</u> GTAGAGGATC GAGATCTCGA T (SEQ ID NO: 39) | AvrII |
| T7T-AvrII: | gc <u>cctagg</u> atccggatatagttcctcct (SEQ ID NO: 40) | AvrII |

The resulted series of pBS-T7nifENX plasmids were cleaved with AvrII and ligated with AvrII-digested pKU7017 as described in Example 1. The ligation products were then transformed into E. coli BL21 (DE3), The transformants were tested in Acetylene Reduction Assay for their nitrogen fixing enzyme activities, as described in Example 1. The results showed that the nitrogen fixing enzyme acticity reached the highest level when the promoter of nifENX was changed to T7M5.

By comparing the strength of each nif promoter (Table 4) with the strengths of different T7 variants reported by Diane Imburgio (supra), it can be seen that the relative strength of T7M5 (0.49) and the relative strength of nifENX promoter (0.43) was around the same level.

3.5 Replacement of the Promoters of Other nif Genes

The promoters of other nif genes were replaced with T7 promoters of different strengths based on the determined β-galactosidase, activities. The following plasmids were selected after testing:

pKU7021: pet28aT7M6+nifF
pKU7023: pet28aT7wt+nifHDKY
pKU7026: pet28aT7M6+nifBQ
pKU7027: pet28aT7wt+nifJ
pKU7051: pet28aT7M5+nifUSVM 3.6 Construction of pKU7180 and pKU7181 and Determination of Their Nitrogen Fixing Enzyme Activity The plasmid pKU7180 was constructed by replacement of the promoters of all nif operons into T7 promoters. The plasmid pKU7181 was constructed in the same way except that it does not contain nifLA.

pKU7180 and pKU7181 plasmids were used to transform E. coli BL21 (DE3) respectively. The nitrogen fixing enzymes activities of the transformants induced with different concentrations of IPTG were determined in Acetylene Reduction Assay, as described in Example 1.

TABLE 8

The induced nitrogen fixing enzyme activities

| Bacterial Strain | nif Genotype | Nitrogen Fixing Enzyme activity nmol $C_2H_4$/min/mg protein | | | |
|---|---|---|---|---|---|
| | | IPTG0 (mM) | IPTG0.05 | IPTG0.1 | IPTG1.0 |
| JM109 (pKU7180 + pKU7100) | nif+/ ΔnifLA | 8.0 | 156.4 | 302.8 | 254.8 |
| JM109 (pKU7181 + pKU7100) | nif+ | 8.35 | 177.8 | 621 | 520 |

Example 4

Construction of Plasmid pKU7100

The plasmid pKU7100 was constructed by cloning of T7 RNA polymerase into a multicopy plasmid pBR322 to express T7 RNA polymerase at a high level.

Taking pBR322 as a temple, the following primers were used to perform PCR as described in Example 1 to create an NcoI restriction site. The expression of T7 RNA polymerase is thus driven by the promoter of the tetracycline-resistance gene of pBR322. The procedure was as described in Example 1.

TABLE 9

| Primer Name | Primer Sequence (5'-3') |
|---|---|
| pBR322-1: | acgcagtcaggcaccgtCCatgGaatctaacaatgcgctc (SEQ ID NO: 41) |
| pBR322-2: | GAGCGCATTGTTAGATTCCATGGACGGTGCCTGACTGCGT (SEQ ID NO: 42) |

The T7 RNA polymerase was amplified by PCR as described in Example 1, using the chromosomal of *E. coli* BL21 (DE3) as the template. The primers are as follows.

TABLE 10

| Primer Name | Primer Sequence (5'-3') | Restriction Site |
|---|---|---|
| T7pol-1: | catg CCATGG acacga ttaacatcgc (SEQ ID NO: 43) | NcoI |
| T7pol-2: | cgc GGATCCT TATTACGCGA ACGCGAAGT (SEQ ID NO: 44) | HindIII |

The PCR product of T7 RNA polymerase was digested with NcoI and BamHI and ligated with the mutated pBR322 plasmid that was also digested with NcoI and BamHI. The resulted plasmid was named pKU7100. This plasmid was used to transform *E. coli* as described in Example 1 and positive clones were verified.

Example 5

Determination of Nitrogen Fixing Enzyme Activity

*E. coli* JM109 cells were transformed with plasmids pKU7180 and pKU7181 respectively and were induced to be competent. After transformed with pKU7100 and induced with IPTG in different concentrations, the nitrogen fixation enzyme activity was determined in Acetylene Reduction Assays using the above-mentioned methods.

The nitrogen fixation enzyme activity was also determined at different temperatures, and in strains with deletion of NtrC or σ54 factor. The methods are as above-mentioned.

TABLE 11

The effect of temperature and nitrogen availability on nitrogen fixing enzyme activity of *E. coli* strains with different plasmids

| | | Nitrogen Fixing Enzyme Activity: nmol $C_2H_4$/min/mg protein | | | |
|---|---|---|---|---|---|
| | | Glutamate 20 mM | | $(NH_4)_2SO_4$ 20 mM | |
| Bacterial Strain | nif Genotype | 30° C. | 37° C. | 30° C. | 37° C. |
| JM109 (pKU7017) | nif+ | 229.2 | 8.0 | 0 | 0 |
| BL21 (pKU7180) | nif+ | 31.4 | 18.0 | 19.2 | 7.2 |
| JM109 (pKU7180 + pKU7100) | nif+ | 302.8 | 96.4 | 391.6 | 13.7 |

TABLE 12

The effect of NtrC and σ54 factor on nitrogen fixing enzyme activity

| Bacterial Strain | Corresponding Genotype | Nitrogen Fixing Enzyme Activity: nmol $C_2H_4$/min/mg protein |
|---|---|---|
| JM109 (pKU7100 + pKU7180) | WT | 302 |
| TH1 (pKU7100 + pKU7180) | σ54⁻ | 90 |
| TH1 (pKU7017) | σ54⁻ | 0 |
| WJ9 (pKU7100 + pKU7180) | NtrC⁻ | 109.6 |
| WJ9 (pKU7017) | NtrC⁻ | 0 |

It can be seen that by replacement of the promoters, the nitrogen fixation enzyme activity is no longer regulated by σ54, NtrC, NifA, temperature, and nitrogen availability; instead, it is now only induced by a single small molecule (IPTG). An expression island is thus formed, which makes the regulation of the expression system more simple.

The invention claimed is:

1. An expression island comprising multiple prokaryotic nitrogen fixation genes and multiple T7 promoters but does not contain a natural promoter of said prokaryotic genes for nitrogen fixation, wherein each T7 promoter regulates one or more of said genes, and wherein the relative strength of the natural promoter and that of the T7 promoter are around the same level, wherein said multiple T7 promoters comprise T7M6, and said genes comprise nifF, nifB, and nifQ.

2. The expression island of claim 1, wherein said multiple T7 promoters further comprise the promoters selected from the group consisting of T7wt, T7M4, T7M5, T7M7, T7M8, and T7 variant that has promoter activity.

3. The expression island of claim 1, wherein said multiple genes are presented in the form of natural operons.

4. A plasmid comprising the expression island of claim 1.

5. An expression system comprising the plasmid of claim 4 and a multicopy plasmid comprising T7 RNA polymerase genes.

6. A cell comprising the expression island of claim 1.

7. The expression island of claim 3, wherein one operon contains a restriction site different from other operons.

8. The expression island of claim 1, wherein said genes further comprise the genes selected from the group consisting of nifJ, nifH, nifD, nifK, nifE, nifN, nifU, nifS, nifV, nifM, nifX and NifY.

9. The plasmid of claim 4, wherein said plasmid is a multicopy plasmid.

10. A cell comprising the plasmid of claim 4.

11. A cell comprising the expression system of claim 5.

12. The expression island of claim 7, wherein the operons comprise T7M6+nifF and T7M6+nifBQ.

13. The expression island of claim 12, wherein the expression island further comprises the operons selected from the group consisting of T7wt+nifJ, T7wt+nifHDKY, T7M5+nifENX, T7M5+nifUSVM.

* * * * *

SEQUENCE LISTING

<160> NUMBER OF SEQ ID NOS: 47

<210> SEQ ID NO 1
<211> LENGTH: 49
<212> TYPE: DNA
<213> ORGANISM: artificial
<220> FEATURE:
<223> OTHER INFORMATION: NifHDKY(1) primer sequence

<400> SEQUENCE: 1
gcagaattcg cggccgctct agatacgtat gaagagagtc gccgcgcag      49

<210> SEQ ID NO 2
<211> LENGTH: 49
<212> TYPE: DNA
<213> ORGANISM: artificial
<220> FEATURE:
<223> OTHER INFORMATION: NifH DKY(2) primer sequence

<400> SEQUENCE: 2
gctctgcagg cggccgacta gttacgtagc aacaagcaca aaacaggga      49

<210> SEQ ID NO 3
<211> LENGTH: 49
<212> TYPE: DNA
<213> ORGANISM: artificial
<220> FEATURE:
<223> OTHER INFORMATION: NifJ(1) primer sequence

<400> SEQUENCE: 3
gcagaattcg cggccgctct agaagtactg ttatttgtcg ccgcgcagg          49

<210> SEQ ID NO 4
<211> LENGTH: 49
<212> TYPE: DNA
<213> ORGANISM: artificial
<220> FEATURE:
<223> OTHER INFORMATION: NifJ(2) primer sequence

<400> SEQUENCE: 4
gctctgcagg cggccgacta gtagtactct aaaggcccgc tactcctcg          49

<210> SEQ ID NO 5
<211> LENGTH: 51
<212> TYPE: DNA
<213> ORGANISM: artificial
<220> FEATURE:
<223> OTHER INFORMATION: NifUSVM(1) primer sequence

<400> SEQUENCE: 5
gcagaattcg cggccgctct agagtttaaa cgcaggagca ggagtggcat g          51

<210> SEQ ID NO 6
<211> LENGTH: 50
<212> TYPE: DNA
<213> ORGANISM: artificial
<220> FEATURE:
<223> OTHER INFORMATION: NifUSVM(2) primer sequence

<400> SEQUENCE: 6
gctctgcagg cggccgacta gtgtttaaac cgaggctacc cgcacagtcc          50

<210> SEQ ID NO 7
<211> LENGTH: 49
<212> TYPE: DNA
<213> ORGANISM: artificial
<220> FEATURE:
<223> OTHER INFORMATION: NifENX(1) primer sequence

<400> SEQUENCE: 7
gcagaattcg cggccgctct agacctaggg cttcttgatg cgcctaacc          49

<210> SEQ ID NO 8
<211> LENGTH: 49
<212> TYPE: DNA
<213> ORGANISM: artificial
<220> FEATURE:
<223> OTHER INFORMATION: NifENX(2) primer sequence

<400> SEQUENCE: 8
gctctgcagg cggccgacta gtcctagggt cacagaaacg acacggcta          49

<210> SEQ ID NO 9
<211> LENGTH: 49
<212> TYPE: DNA
<213> ORGANISM: artificial
<220> FEATURE:

```
<223> OTHER INFORMATION: NifLA(1) primer sequence

<400> SEQUENCE: 9
gcagaattcg cggccgctct agacttaagt gttgcgctcc tgtcggaaa        49

<210> SEQ ID NO 10
<211> LENGTH: 50
<212> TYPE: DNA
<213> ORGANISM: artificial
<220> FEATURE:
<223> OTHER INFORMATION: NifLA(2) primer sequence

<400> SEQUENCE: 10
gctctgcagg cggccgacta gtcttaagac agtcgcggca tggtgatatc       50

<210> SEQ ID NO 11
<211> LENGTH: 49
<212> TYPE: DNA
<213> ORGANISM: artificial
<220> FEATURE:
<223> OTHER INFORMATION: NifBQ(1) primer sequence

<400> SEQUENCE: 11
gcagaattcg cggccgctct agagctagcc gactgtgaag ccttatgtg        49

<210> SEQ ID NO 12
<211> LENGTH: 48
<212> TYPE: DNA
<213> ORGANISM: artificial
<220> FEATURE:
<223> OTHER INFORMATION: NifBQ(2) primer sequence

<400> SEQUENCE: 12
gctctgcagg cggccgacta gtgctagcgc tactcaaaac aggcgctg         48

<210> SEQ ID NO 13
<211> LENGTH: 51
<212> TYPE: DNA
<213> ORGANISM: artificial
<220> FEATURE:
<223> OTHER INFORMATION: NifF(1) primer sequence

<400> SEQUENCE: 13
gcagaattcg cggccgctct agaatttaaa tttcagggtc atcgcaaact c      51

<210> SEQ ID NO 14
<211> LENGTH: 51
<212> TYPE: DNA
<213> ORGANISM: artificial
<220> FEATURE:
<223> OTHER INFORMATION: NifF(2) primer sequence

<400> SEQUENCE: 14
gctctgcagg cggccgacta gtatttaaat gttaacgcct acagcacggt g      51

<210> SEQ ID NO 15
<211> LENGTH: 18
<212> TYPE: DNA
<213> ORGANISM: artificial
<220> FEATURE:
<223> OTHER INFORMATION: primer M13F

<400> SEQUENCE: 15
gtaaaacgac ggccagtg                                          18
```

<210> SEQ ID NO 16
<211> LENGTH: 19
<212> TYPE: DNA
<213> ORGANISM: artificial
<220> FEATURE:
<223> OTHER INFORMATION: primer M13R

<400> SEQUENCE: 16
ggaaacagct atgaccatg                                                19

<210> SEQ ID NO 17
<211> LENGTH: 35
<212> TYPE: DNA
<213> ORGANISM: artificial
<220> FEATURE:
<223> OTHER INFORMATION: T7M4(1) primer sequence

<400> SEQUENCE: 17
gaaattaata cgactcacaa taggggaatt gtgag                              35

<210> SEQ ID NO 18
<211> LENGTH: 35
<212> TYPE: DNA
<213> ORGANISM: artificial
<220> FEATURE:
<223> OTHER INFORMATION: T7M4(2) primer sequence

<400> SEQUENCE: 18
ctcacaattc ccctattgtg agtcgtatta atttc                              35

<210> SEQ ID NO 19
<211> LENGTH: 35
<212> TYPE: DNA
<213> ORGANISM: artificial
<220> FEATURE:
<223> OTHER INFORMATION: T7M5(1) primer sequence

<400> SEQUENCE: 19
attaatacga ctcactagag gggaattgtg agcgg                              35

<210> SEQ ID NO 20
<211> LENGTH: 35
<212> TYPE: DNA
<213> ORGANISM: artificial
<220> FEATURE:
<223> OTHER INFORMATION: T7M5(2) primer sequence

<400> SEQUENCE: 20
ccgctcacaa ttcccctcta gtgagtcgta ttaat                              35

<210> SEQ ID NO 21
<211> LENGTH: 35
<212> TYPE: DNA
<213> ORGANISM: artificial
<220> FEATURE:
<223> OTHER INFORMATION: T7M6(1) primer sequence

<400> SEQUENCE: 21
aaattaatac gactcacgat aggggaattg tgagc                              35

<210> SEQ ID NO 22
<211> LENGTH: 35
<212> TYPE: DNA
<213> ORGANISM: artificial
<220> FEATURE:
<223> OTHER INFORMATION: T7M6(2) primer sequence

<400> SEQUENCE: 22
gctcacaatt ccctatcgt gagtcgtatt aattt                35

<210> SEQ ID NO 23
<211> LENGTH: 35
<212> TYPE: DNA
<213> ORGANISM: artificial
<220> FEATURE:
<223> OTHER INFORMATION: T7M7(1) primer sequence

<400> SEQUENCE: 23
ccctatagtg agtcgtaata atttcgcggg atcga                35

<210> SEQ ID NO 24
<211> LENGTH: 35
<212> TYPE: DNA
<213> ORGANISM: artificial
<220> FEATURE:
<223> OTHER INFORMATION: T7M7(2) primer sequence

<400> SEQUENCE: 24
tcgatcccgc gaaattatta cgactcacta taggg                35

<210> SEQ ID NO 25
<211> LENGTH: 35
<212> TYPE: DNA
<213> ORGANISM: artificial
<220> FEATURE:
<223> OTHER INFORMATION: T7M8(1) primer sequence

<400> SEQUENCE: 25
ccctatagtg agtcgtacta atttcgcggg atcga                35

<210> SEQ ID NO 26
<211> LENGTH: 35
<212> TYPE: DNA
<213> ORGANISM: artificial
<220> FEATURE:
<223> OTHER INFORMATION: T7M8(2) primer sequence

<400> SEQUENCE: 26
tcgatcccgc gaaattagta cgactcacta taggg                35

<210> SEQ ID NO 27
<211> LENGTH: 29
<212> TYPE: DNA
<213> ORGANISM: artificial
<220> FEATURE:
<223> OTHER INFORMATION: T7NifHDKY(1) primer sequence

<400> SEQUENCE: 27
gctctagaca ctcaacaaca ggagaagtc                29

<210> SEQ ID NO 28
<211> LENGTH: 33
<212> TYPE: DNA
<213> ORGANISM: artificial
<220> FEATURE:
<223> OTHER INFORMATION: T7NifHDKY(2) primer sequence

<400> SEQUENCE: 28
cccaagcttg caacaagcac aaaacaggga tta                33

<210> SEQ ID NO 29
<211> LENGTH: 28

<210> SEQ ID NO 29
<211> LENGTH: 28
<212> TYPE: DNA
<213> ORGANISM: artificial
<220> FEATURE:
<223> OTHER INFORMATION: T7NifJ(1) primer sequence

<400> SEQUENCE: 29
gctctagaca actgggtttg ccgcttat                                28

<210> SEQ ID NO 30
<211> LENGTH: 29
<212> TYPE: DNA
<213> ORGANISM: artificial
<220> FEATURE:
<223> OTHER INFORMATION: T7NifJ(2) primer sequence

<400> SEQUENCE: 30
cccaagcttc ctgctggata cgctgctta                               29

<210> SEQ ID NO 31
<211> LENGTH: 28
<212> TYPE: DNA
<213> ORGANISM: artificial
<220> FEATURE:
<223> OTHER INFORMATION: T7NifUSVM(1) primer sequence

<400> SEQUENCE: 31
gctctagatg aaccgcgccc cggcgttt                                28

<210> SEQ ID NO 32
<211> LENGTH: 29
<212> TYPE: DNA
<213> ORGANISM: artificial
<220> FEATURE:
<223> OTHER INFORMATION: T7NifUSVM(2) primer sequence

<400> SEQUENCE: 32
cccaagcttc gaggctaccc gcacagtcc                               29

<210> SEQ ID NO 33
<211> LENGTH: 28
<212> TYPE: DNA
<213> ORGANISM: artificial
<220> FEATURE:
<223> OTHER INFORMATION: T7NifENX(1) primer sequence

<400> SEQUENCE: 33
gctctagacc tcatccccca ccgtcaac                                28

<210> SEQ ID NO 34
<211> LENGTH: 29
<212> TYPE: DNA
<213> ORGANISM: artificial
<220> FEATURE:
<223> OTHER INFORMATION: T7NifENX(2) primer sequence

<400> SEQUENCE: 34
cccaagcttg gatgttgacg gaaaacgcc                               29

<210> SEQ ID NO 35
<211> LENGTH: 28
<212> TYPE: DNA
<213> ORGANISM: artificial
<220> FEATURE:
<223> OTHER INFORMATION: T7NifBQ(1) primer sequence

<400> SEQUENCE: 35
gctctagagg tatcgcccaa ccacgaag                                                      28

<210> SEQ ID NO 36
<211> LENGTH: 29
<212> TYPE: DNA
<213> ORGANISM: artificial
<220> FEATURE:
<223> OTHER INFORMATION: T7NifBQ(2) primer sequence

<400> SEQUENCE: 36
cccaagcttc gaagacgtcg cataatcac                                                     29

<210> SEQ ID NO 37
<211> LENGTH: 28
<212> TYPE: DNA
<213> ORGANISM: artificial
<220> FEATURE:
<223> OTHER INFORMATION: T7NifF(1) primer sequence

<400> SEQUENCE: 37
gctctagagc gagaacgcgt attttcaa                                                      28

<210> SEQ ID NO 38
<211> LENGTH: 29
<212> TYPE: DNA
<213> ORGANISM: artificial
<220> FEATURE:
<223> OTHER INFORMATION: T7NifF(2) primer sequence

<400> SEQUENCE: 38
cccaagcttc tacagcacgg tgcgtttaa                                                     29

<210> SEQ ID NO 39
<211> LENGTH: 29
<212> TYPE: DNA
<213> ORGANISM: artificial
<220> FEATURE:
<223> OTHER INFORMATION: T7P-AvrII primer sequence

<400> SEQUENCE: 39
gccctagggt agaggatcga gatctcgat                                                     29

<210> SEQ ID NO 40
<211> LENGTH: 28
<212> TYPE: DNA
<213> ORGANISM: artificial
<220> FEATURE:
<223> OTHER INFORMATION: T7T-AvrII primer sequence

<400> SEQUENCE: 40
gccctaggat ccggatatag ttcctcct                                                      28

<210> SEQ ID NO 41
<211> LENGTH: 40
<212> TYPE: DNA
<213> ORGANISM: artificial
<220> FEATURE:
<223> OTHER INFORMATION: pBR322-1 primer sequence

<400> SEQUENCE: 41
acgcagtcag gcaccgtcca tggaatctaa caatgcgctc                                         40

<210> SEQ ID NO 42
<211> LENGTH: 40
<212> TYPE: DNA
<213> ORGANISM: artificial

```
<220> FEATURE:
<223> OTHER INFORMATION: pBR322-2 primer sequence

<400> SEQUENCE: 42
gagcgcattg ttagattcca tggacggtgc ctgactgcgt                          40

<210> SEQ ID NO 43
<211> LENGTH: 26
<212> TYPE: DNA
<213> ORGANISM: artificial
<220> FEATURE:
<223> OTHER INFORMATION: T7pol-1 primer sequence

<400> SEQUENCE: 43
catgccatgg acacgattaa catcgc                                         26

<210> SEQ ID NO 44
<211> LENGTH: 29
<212> TYPE: DNA
<213> ORGANISM: artificial
<220> FEATURE:
<223> OTHER INFORMATION: T7pol-2 primer sequence

<400> SEQUENCE: 44
cgcggatcct tattacgcga acgcgaagt                                      29

<210> SEQ ID NO 45
<211> LENGTH: 49
<212> TYPE: DNA
<213> ORGANISM: artificial
<220> FEATURE:
<223> OTHER INFORMATION: prefix sequence

<400> SEQUENCE: 45
gcagaattcg cggccgcttc tagagtacta gtagcggccg ctgcaggct                49

<210> SEQ ID NO 46
<211> LENGTH: 49
<212> TYPE: DNA
<213> ORGANISM: artificial
<220> FEATURE:
<223> OTHER INFORMATION: postfix sequence

<400> SEQUENCE: 46
cgtcttaagc gccggcgaac atctcatgat catcgccggc gacgtccga                49

<210> SEQ ID NO 47
<211> LENGTH: 23
<212> TYPE: DNA
<213> ORGANISM: artificial
<220> FEATURE:
<223> OTHER INFORMATION: T7 promoter sequence

<400> SEQUENCE: 47
taatacgact cactataggg aga                                            23
```